US008283478B2

(12) United States Patent
Abdel-Magid et al.

(10) Patent No.: US 8,283,478 B2
(45) Date of Patent: Oct. 9, 2012

(54) PROCESS FOR PREPARATION OF SULFAMIDE DERIVATIVES

(75) Inventors: Ahmed F. Abdel-Magid, Ambler, PA (US); Steven J. Mehrman, Quakertown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 292 days.

(21) Appl. No.: 11/406,794

(22) Filed: Apr. 19, 2006

(65) Prior Publication Data

US 2006/0270856 A1    Nov. 30, 2006

Related U.S. Application Data

(60) Provisional application No. 60/683,151, filed on May 20, 2005.

(51) Int. Cl.
C07D 333/58 (2006.01)
C07D 493/14 (2006.01)
C07D 307/81 (2006.01)

(52) U.S. Cl. .......... 548/567; 549/58; 549/387; 549/467; 564/79

(58) Field of Classification Search ............. 549/58, 549/387, 467; 548/567; 564/79
See application file for complete search history.

(56) References Cited

U.S. PATENT DOCUMENTS

| | | |
|---|---|---|
| 2,527,861 A | 10/1950 | Walter |
| 3,143,549 A | 8/1964 | Lafferty et al. |
| 3,318,952 A | 5/1967 | Houlihan |
| 3,383,414 A | 5/1968 | Houlihan |
| 3,539,573 A | 11/1970 | Schmutz |
| 3,621,096 A | 11/1971 | Prange et al. |
| 4,513,006 A | 4/1985 | Maryanoff et al. |
| 4,539,413 A | 9/1985 | Mouzin et al. |
| 4,710,500 A | 12/1987 | Perregaard |
| 4,804,663 A | 2/1989 | Kennis et al. |
| 4,831,031 A | 5/1989 | Lowe, III et al. |
| 4,879,288 A | 11/1989 | Warawa et al. |
| 5,112,838 A | 5/1992 | Perregaard et al. |
| 5,158,952 A | 10/1992 | Janssen et al. |
| 5,192,785 A | 3/1993 | Lo et al. |
| 5,194,446 A | 3/1993 | Lo et al. |
| 5,212,326 A | 5/1993 | Meade |
| 5,229,382 A | 7/1993 | Chakrabarti et al. |
| 5,238,945 A | 8/1993 | Perregaard et al. |
| 5,242,942 A | 9/1993 | Costanzo et al. |
| 5,258,402 A | 11/1993 | Maryanoff |
| 5,273,993 A | 12/1993 | Lo et al. |
| 5,312,925 A | 5/1994 | Allen et al. |
| 5,384,327 A | 1/1995 | Costanzo et al. |
| 5,387,700 A | 2/1995 | Maryanoff et al. |
| 5,731,348 A | 3/1998 | Gu |
| 5,753,693 A | 5/1998 | Shank |
| 5,753,694 A | 5/1998 | Shank |
| 5,760,007 A | 6/1998 | Shank et al. |
| 5,780,650 A | 7/1998 | Furukawa et al. |
| 5,935,933 A | 8/1999 | Shank et al. |
| 5,998,380 A | 12/1999 | Ehrenberg et al. |
| 6,071,537 A | 6/2000 | Shank |
| 6,150,419 A | 11/2000 | Fairbanks et al. |
| 6,187,338 B1 | 2/2001 | Caruso et al. |
| 6,191,163 B1 | 2/2001 | Cottrell |
| 6,211,241 B1 | 4/2001 | Islam et al. |
| 6,319,903 B1 | 11/2001 | Carrazana et al. |
| 6,322,503 B1 | 11/2001 | Sparhawk, Jr. |
| 6,323,236 B2 | 11/2001 | McElroy |
| 6,391,877 B1 | 5/2002 | Islam et al. |
| 6,503,884 B1 | 1/2003 | Ehrenberg et al. |
| 6,559,293 B1 | 5/2003 | Almarsson et al. |
| 6,562,865 B1 | 5/2003 | Codd et al. |
| 6,583,172 B1 | 6/2003 | Shank |
| 6,627,653 B2 | 9/2003 | Plata-Salaman et al. |
| 6,852,701 B2 | 2/2005 | Plata-Salaman et al. |
| 6,852,738 B2 | 2/2005 | Jones et al. |
| 6,949,518 B1 | 9/2005 | Chu et al. |
| 2001/0008889 A1 | 7/2001 | Caruso et al. |
| 2002/0015713 A1 | 2/2002 | Murdock et al. |
| 2004/0073037 A1 | 4/2004 | Jones |
| 2004/0192690 A1 | 9/2004 | Buxton et al. |
| 2004/0253223 A1 | 12/2004 | Rodriguez |
| 2005/0148603 A1 | 7/2005 | Jimenez et al. |
| 2005/0282887 A1 | 12/2005 | McComsey et al. |
| 2006/0041008 A1 | 2/2006 | McComsey et al. |
| 2006/0047001 A1* | 3/2006 | Parker et al. .......... 514/419 |
| 2006/0241172 A1 | 10/2006 | Zhou et al. |
| 2006/0270856 A1 | 11/2006 | Abdel-Magid et al. |
| 2006/0276528 A1 | 12/2006 | Magid et al. |
| 2007/0155821 A1 | 7/2007 | Smith-Swintosky |
| 2007/0155822 A1 | 7/2007 | Smith-Swintosky et al. |
| 2007/0155823 A1 | 7/2007 | Smith-Swintosky et al. |
| 2007/0155824 A1 | 7/2007 | Smith-Swintosky |
| 2007/0155825 A1 | 7/2007 | Smith-Swintosky et al. |

(Continued)

FOREIGN PATENT DOCUMENTS

CA    2416647 A    1/2003

(Continued)

OTHER PUBLICATIONS

PCT International Search Report, PCT/US2006/014766, Sep. 12, 2006.
Weiss, G. et al.: "Herstellung und Reaktionen von N-Monoalkylamidosulfonylchloriden" Liebigs Annalen Der Chemie, vol. 729, Dec. 1969, pp. 40-51, XP002187581.
Maryanoff, B.E.et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1998, pp. 1315-1343, XPOO2149867.
Maryanoff, B.E. et al.: "Comparison of Sulphamate and Sulphamide Groups for the Inhibition of Carbonic Anhydrase-II by Using Topiramate as a Structural Platform". Journal Of Medicinal Chemistry, vol. 48, No. 6, Dec. 13, 2004, pp. 1941-1947, XP002345002.
Kohno, H. et al.: "A Novel Synthesis of Isoquinolines Containing an Electron Withdrawing Substitute". Heterocycles, vol. 51, No. 1, 1999, pp. 103-117, XP008052600.

(Continued)

Primary Examiner — Bernard Dentz
(74) Attorney, Agent, or Firm — Hal Brent Woodrow

(57) ABSTRACT

The present invention is directed to novel process for the preparation of sulfonylimine and sulfamide derivatives.

5 Claims, No Drawings

U.S. PATENT DOCUMENTS

| | | | |
|---|---|---|---|
| 2007/0155826 A1 | 7/2007 | Smith-Swintosky et al. |
| 2007/0155827 A1 | 7/2007 | Smith-Swintosky et al. |
| 2007/0191449 A1 | 8/2007 | Smith-Swintosky |
| 2007/0191450 A1 | 8/2007 | Smith-Swintosky |
| 2007/0191451 A1 | 8/2007 | Smith-Swintosky |
| 2007/0191452 A1 | 8/2007 | Smith-Swintosky |
| 2007/0191453 A1 | 8/2007 | Smith-Swintosky |
| 2007/0191459 A1 | 8/2007 | Smith-Swintosky |
| 2007/0191460 A1 | 8/2007 | Smith-Swintosky |
| 2007/0191461 A1 | 8/2007 | Smith-Swintosky |
| 2007/0191474 A1 | 8/2007 | Smith-Swintosky |
| 2007/0232685 A1 | 10/2007 | Fawzy et al. |
| 2007/0293440 A1 | 12/2007 | Smith-Swintosky et al. |
| 2007/0293476 A1 | 12/2007 | Smith-Swintosky et al. |
| 2008/0027131 A1 | 1/2008 | Smith-Swintosky et al. |
| 2009/0209634 A1 | 8/2009 | Smith-Swintosky |
| 2009/0247616 A1 | 10/2009 | Smith-Swintosky |
| 2009/0318544 A1 | 12/2009 | Mehrman et al. |
| 2010/0063138 A1 | 3/2010 | Mccomsey et al. |

FOREIGN PATENT DOCUMENTS

| | | |
|---|---|---|
| DE | 1211166 | 2/1966 |
| DE | 2022370 | 12/1971 |
| DK | 9800727 A | 5/1998 |
| EP | 0138441 | 4/1985 |
| EP | 0483881 | 5/1992 |
| EP | 490689 | 6/1992 |
| EP | 0498770 | 8/1992 |
| EP | 503440 A1 | 9/1992 |
| EP | 478954 | 10/2000 |
| EP | 1056733 | 12/2000 |
| EP | 1118610 | 7/2001 |
| GB | 1087602 | 10/1967 |
| GB | 1111706 | 5/1968 |
| RU | 2226357 | 4/2004 |
| RU | 2246727 | 8/2004 |
| WO | 94/14827 A1 | 7/1994 |
| WO | 95/17406 A1 | 6/1995 |
| WO | 96/06822 A1 | 3/1996 |
| WO | 97/13510 A1 | 4/1997 |
| WO | 97/19682 | 6/1997 |
| WO | 97/19919 | 6/1997 |
| WO | 97/35584 A1 | 10/1997 |
| WO | 98/00123 | 1/1998 |
| WO | 98/00124 A1 | 1/1998 |
| WO | 98/00130 A2 | 1/1998 |
| WO | 98/00131 A1 | 1/1998 |
| WO | 98/06708 A1 | 2/1998 |
| WO | 98/07447 A1 | 2/1998 |
| WO | 98/15270 | 4/1998 |
| WO | 99/44581 A2 | 9/1999 |
| WO | 99/62522 | 12/1999 |
| WO | 00/01376 A2 | 1/2000 |
| WO | 00/07583 A2 | 2/2000 |
| WO | 00/42995 A2 | 7/2000 |
| WO | 00/42996 A2 | 7/2000 |
| WO | 00/49017 | 8/2000 |
| WO | 00/50020 A2 | 8/2000 |
| WO | 00/54588 A1 | 9/2000 |
| WO | 00/61137 | 10/2000 |
| WO | 00/61139 A1 | 10/2000 |
| WO | 00/61140 A1 | 10/2000 |
| WO | 00/66109 A2 | 11/2000 |
| WO | 00/76493 A1 | 12/2000 |
| WO | 01/13904 A2 | 3/2001 |
| WO | 01/76576 A2 | 10/2001 |
| WO | 02/03984 | 1/2002 |
| WO | 02/07821 | 1/2002 |
| WO | 02/09694 | 2/2002 |
| WO | 02/30881 | 4/2002 |
| WO | 02/089785 | 11/2002 |
| WO | 02/096424 | 12/2002 |
| WO | 2004/014352 | 2/2004 |
| WO | 2004/093912 A1 | 4/2004 |
| WO | 2004/092116 A1 | 10/2004 |
| WO | 2004/096771 A1 | 11/2004 |
| WO | 2004/098584 A1 | 11/2004 |
| WO | 2005/020917 A2 | 3/2005 |
| WO | 2006/007435 | 1/2006 |
| WO | 2006/007436 | 1/2006 |
| WO | 2006/010008 A1 | 1/2006 |
| WO | 2006/010750 A1 | 2/2006 |
| WO | 2006/023861 | 3/2006 |
| WO | WO 2006/023861 | 3/2006 |
| WO | 2006/127184 | 11/2006 |
| WO | 2007/075695 | 7/2007 |
| WO | 2007/075698 | 7/2007 |
| WO | 2007/075717 | 7/2007 |
| WO | 2007/075751 | 7/2007 |
| WO | 2007/075752 | 7/2007 |
| WO | 2007/075833 | 7/2007 |
| WO | 2007/075834 | 7/2007 |
| WO | 2007/092086 | 8/2007 |
| WO | 2007/095615 | 8/2007 |
| WO | 2007/095618 | 8/2007 |
| WO | 2007/098486 | 8/2007 |
| WO | 2007/137167 | 11/2007 |
| WO | 2009/089210 | 7/2009 |
| WO | 2009/120191 | 10/2009 |
| WO | 2009/120192 | 10/2009 |

OTHER PUBLICATIONS

Vandi, A., et al.: "Synthesis and Properties of Some N-Substituted Sulphamides", Journal of Organic Chemistry, vol. 26, No. 4, Apr. 1961, pp. 1136-1138, XP002394144.

Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.

Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, Apr. 15, 1996, pp. 2859-2862, XP004029817.

Ten Have, R. et al.:"Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.

Traube, W. et al.:"Zur Kenntnis des Sulfamids". Berichte der Deutschen Chemischen Gesellschaft, vol. 56, 1923, pp. 656-1663, XP002393747.

Huisman, M. et al.:"Synthesis of N-(diemthylsulphamoyl)aldimines, a new type of aldimine derivative". Synthetic Communications, vol. 27, No. 6, 1997, pp. 945-952, XP008067473.

Drach, B.S. et al.:"N-1,2,2,2,-tetra-chloroethyl-N',N'-dimethylsulphamide". Journal of Organic Chemistry of the USSR., vol. 13, No. 7, Jul. 1977, pp. 1289-1294, XP008067470.

Ziegler, E., et al.:"Zur Reaktivitat von C=Ndoppelbindingssytemen, VI. Reaktionen mit Sulfonamiden und Sulfamiden". Zeitschrift Fur Naturforschung, vol. 30B, 1975, pp. 951-953, XP008067475.

Pedras, M. et al.:"Toward the control of *Leptosphaeria maculans*" Design, Synthesis, biological activity, and metabolism of potential detoxification inhibitors of the crucifer phytoalexin brassinin. Bioorganic & Medicinal Chemistry, vol. 14, No. 14, Apr. 17, 2006, pp. 4958-4979, XP005458688.

Swinyard EA, Woodhead JH, White HS, Franklin MR. Experimental selection, quantification, and evaluation of anticonvulsants. In Levy RH, et al., eds.*Antiepileptic Drugs*. 3$^{rd}$ ed. New York: Raven Press, 1989:85-102.

U.S. Appl. No. 12/055,695, Ahmed Abdel-Magid et al.

U.S. Appl. No. 12/055,924, Scott Ballentine et al.

U.S. Appl. No. 12/349,184, Ahmed Abdel-Magid et al.

Maryanoff et al.., J. Med. Chem., vol. 48, No. 6, pp. 1941-1947 (2004).

Maryanoff et al., J. Med. Chem., vol. 30, No. 5, pp. 880-887 (1987).

Nies et al., Goodman & Gilman's The Pharmacological Basis of Therapeutics, 9th Edition, pp. 43-62, 1996.

Notice of Allowance mailed Dec. 31, 2008 in U.S. Appl. No. 11/154,443.

Notice of Allowance mailed Jun. 8, 2009 in U.S. Appl. No. 11/154,443.

Notice of Allowance mailed Oct. 9, 2009 in U.S. Appl. No. 11/154,443.

Notice of Allowance mailed Oct. 30, 2008 in U.S. Appl. No. 11/209,122.
Notice of Allowance mailed Sep. 24, 2009 in U.S. Appl. No. 11/209,122.
Office Action mailed Jul. 9, 2008 in U.S. Appl. No. 11/154,386.
Notice of Allowance mailed Mar. 6, 2009 in U.S. Appl. No. 11/154,386.
Notice of Allowance mailed Sep. 10, 2009 in U.S. Appl. No. 11/154,386.
Chaplan SR et al: "Quantitative assessment of tactile allodynia in the rat paw". J Neurosci Meth, 53:55-63, 1994.
Crooke et al, Abstract, Topiramate Improves Glycemic Control Independent of Weight Loss in ob/ob Mice.diabetes. A Journal of the American Diabetes Association, Abstract Book 61$^{st}$ Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, a Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dickenson et al. Neurobiology of neuropathic pain: mode of action of anticonvulsants. European Journal of Pain, 2002, 6 (Suppl. A): 51-60, 2002.
Dinneen S.F., "The Postprandial State: Mechanism of Glucose Intolerance", Diabet Med Aug. 1997;14 Suppl 3:S19-24.
Dressler et al., Benzodiazepine in geriatric patients . . . , Abstract, Anaesthesiologie and reanimation, 1996, vol. 21/5, pp. 136-138.
Drug Facts and Comparison (1995 Edition, pp. 1607).
Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.
Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2000.
Edwards, et al., Evaluation of Topiramate in the Management of Painful Diabetic Neuropathy. Presented at: 18$^{th}$ Annual Meeting of the American Pain Society; 1998, Fort Lauderdale, FL.
Emancipator K., "Laboratory Diagnosis and Monitoring of Diabetes Mellitus", Am J Clin Pathol, 112(5):665-74 1999.
Erfurth, Andreas et al., "Bupropion as add-on strategy in difficult-to-treat bipolar depressive patients", Neuropsychobiology, vol. 45, No. Sup 1, pp. 33-36, 2002.
Fakhoury et al., Epilepsy Behay. Aug. 2007, abstract.
Flatters, Sjl et al: "Acetyl-L-carnitine prevents and reduces paclitaxel-induced painful peripheralneuropathy", Neurosci Lett 397:219-223, 2006.
Gareri, P. et al, Progress in Neurobiology 61, 2000, 353-396.
Garonna, F. et al., "Topiramate in the treatment of overweight/obese binge eaters ADIS Title: Topiramate: therapeutic use; Obesity; in patient with binge eating disorders" International Journal of Neuropsychopharmacology 3(Suppl 1): 299: Jul 2000 XP001030426 Bassano dG Vicenza Italy, whole document.
Ghaemi et al., Soc. of Bio. Psychiatry, (1999) vol. 45, 137-144.
Goldberg R.G., "Prevention of Type 2 Diabetes", Med Clin North Am, 1998 Jul;82(4):805-21.
Gorelick D A, "Pharmacological treatment" Recent Developments in Alcoholism, vol. 11, 1993, p. 413-427, XP00913482 p. 417.
Gorelick et al., Drugs 2004: 64(14), pgs. 1547-1573.
Grond et al., "Weak Opioids—an educational substitute for morphine?", Current Opinion in Anaesthesiology, vol. 11, No. 5, 1998, pp. 559-565 XP00982759.
Groop L., "Characterization of the Prediabetic State", Am J Hypertension; Sep. 1997;10(9 Pt 2):1725-180S.
Guillaume et al., "Glial contribution to seizure: Carbonic anhydrase activity in epileptic mammalian brain" Epilepsia, 1991, vol. 32, No. 1, 1991, pp. 10-15.

Haffner S.M., "Impaired Glucose Tolerance, Insulin Resistance and Cardiovascular Disease", Diabetic Medicine, Aug. 1977;14 Suppl 3:S12-8.
Haffner S.M., "The Prediabetic Problem: Development of Non-Insulin-Dependent Diabetes Mellitus and Related Abnormalities", J Diabetes Complications, Mar-Apr. 1997; 11(2):69-76.
Harrison's Principles of Internal Medicine, Isselbacher et al. eds. McGraw-Hill, Inc., New York, 1994, p. 69.
Harrison'S Principles of Internal Medicine, vol. 2, 23d ed., Ed by Isselbacher, Braunwald, Wilson, Martin, Fauci and Kasper, McGraw-Hill Inc New York City, 1994, p. 2275.
Hatzinger, M. et al., Wien. Med. Wochenschr. 1999, 149, 511-514.
Hauner H, "Managing type 2 diabetes mellitus in patients with obesity," Treatments in Endocrinology, 2004, 3(4), 223-232 (only abstract provided).
Headache Classification Committee of the International Headache Society. Cephalalgia 1988;8 Suppl 7:1-96.
Hering et al., "Sodium valproate in the treatment of cluster headache", Cephalalgia (Sep. 1989) 9(3) pp. 195-198.
Jay et al., "Epilepsy, Migraine and EEG Abnormalities in Children: a Review & Hypothesis," Journal of Head and Face Pain, abstract, vol. 22, Issue 3, pp. 110-114, 1982.
Joffe, R.T. et al., Arch. Gen. Psychiatry 1993, 50, 397-393.
Johns Hopkins Clinical Trial of Topiramate for Cocaine Addiction (ClinicalTrials.gov).
Johnson, B A: "Progress in the development of topiramate for treating alcohol dependence: From a hypothesis to a proof-of-concept study" Alcoholism: Clinical and Experimental Research 2004 United States, vol. 28, No. 8, 2004, pp. 1137-1144.
Johnson, SA CNS Drugs, 2005. vol. 19, No. 1 0, pp. 873-896.
Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.
Keck, P et al, "Valproate and carbamazepine in the treatment of panic and post traumatic stress disorders, withdrawals states . . . " J Clin Psychopharm, vol. 12, No. 1, p36S-p41S.
Kent, J.M., Lancet 2000, 355, 911-918.
Ketter, T.A. et al., J. Clin. Psychiatry 1995, 56, 471-475.
Keung W.M. et al, "Daidzin and daidzein suppress free-choice ethanol intake by Syrian golden hamsters" Proc Natl Acad Sci, vol. 90, p. 1008-10012, Nov. 1993.
Klinger et al., "Inhibition of carbonic anhydrase-II by sulfamate and sulfamide groups: An investigation involving direct thermodynamic binding measurements" Journal of Medicinal Chemistry, vol. 49, No. 12, 15 Jun. 2006, pp. 3496-3500.
Kralinsky E.A. Tramal in the treatment of pain in children with malignancies XP002162259 English Abstract & Klinicka Onkologie, vol. 7, No. 6, 1994, pp. 182-185.
Kunkler et al., "Hippocampal Spreading Depression Bilaterally Activates the Caudal Trigeminal Nucleus in Roadent", Hippocampus 13:835-844 (2003).
Kuzniecky et al., "Topiramate increases cerebral GABA in healthy humans", Neurology (Aug. 1998) 51(2) pp. 627-629.
Kyowa Hakko, "Topiramate" Drugs of the Future, ES, Barcelona, vol. 21, No. 4, Jan. 1, 1996; p. 463-465, XP002043895.
Langtry H.D. et al, "Topiramate, A review of its pharmacodynamic and pharmacokinetic properties and clinical efficacy in the management of epilepsy" Drugs, (1997) 54/5 pp. 752-773, XP002179441.
Lydiard, R.B. et al., J. Clin. Psychiatry 1998, 59, Suppl. 18, 10-17.
Malatynska et al., "Dominant-submissive behavior as models of mania and depression", Neuroscience and Biobehavioral Review, 29 (2005) 715-737.
Malatynska et al., "Submissive behavior in mice as a test for antidepressant drug activity", Neuroscience and Biobehavioral Review, 82 (2005) 306-313.
Mathew, Ninan T., MD, et al, "Prophylaxis of Migraine, Transformed Migraine, and Cluster Headache with Topiramate" Headache (2002), (42)796-803.
Mathew, N. T. "Antiepileptic Drugs in Migraine Prevention", 2001, Headache, Nov./Dec. Suppl 2001, pp. S18-S24.
Mazzotta et al., J Headache Pain, 2004 5:S67-S70.
McElroy, S.L. et al., "A pilot trial of adjunctive topiramate in the treatment of bipolar disorder Adis Title: Topiramate: therapeutic use;

Bipolar disorder: a pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.

Meldrum B. et al., "Excitatory amino acid neurotoxicity and neurodegenerative disease" TIPS, vol. 11, 1990, pp. 379-387, XP000915223.

Mueller T I, "A double-blind, placebo-controlled pilot study of carbamazepine for the treatment of alcohol dependence", Alcoholism Clin Exp Res, vol. 21, No. 1, 1997, p. 86-92, X00913485.

Moller, H.J. et al., Eur. Arch. Psychiatry Clin. Neurosci. 2000, 250, 57-68.

Moskowitz, M.A., "The Neurobiology of Vascular Head Pain", Annals of Neurology, vol. 16, Issue 2, pp. 157-168, 1984.

Mula et al., "The role of anticonvulsant drugs in anxiety disorders: a critical review of the eVidence" Journal of Clinical Psychopharmacology, Williams and Wilkins, vo 1.27, No. 3, 2007, pp. 263-272.

Myers, R.D., "New Drugs for the Treatment of Experimental Alcoholism", Alcohol, vol. 11, No. 6, 1994, p. 439-451.

Nemeroff, C.B., Depress. Anxiety 1996-1997, 4, 169-181.

Olesen et al., "Spreading Cerebral Oligemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).

Olson et al [Editors]. Remington's Pharmaceutical Sciences, pp. 420-425, 1980.

Osborne et al, Abstract, Topiramate Improves Glycemic Control and Triglycerides in Animal Models 1 page The Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.

Ottman et al., "Comorbidity of migraine and epilepsy", Neurology, 1994;44: 2105 (Abstract only).

Pascual D et al: "A cannabinoid agonist, WIN55,212-2, reduces neuropathic nocicipetion induced by paclitaxel in rats" Pain 118:23-34, 2005.

Penovich et al., "Weight Loss in Patients Receiving Topiramate for Intractable Epilepsy", 1994, Neurology 44 (Suppl. 2) Abstract 309P, 46th Annual Meeting of the American Academy of Neurology, Washington, D.C.

Perry et al. "Sumatriptan: An Updated Review of its Use in Migraine", 1998, Drugs, vol. 55, No. 6, pp. 889-922.

Pini et al., "Anti-Epileptic Drugs in the Preventive Treatment of Migraine Headache: a Brief Review", (J. Headache Pain, 2001, 2:13-19.

Polomano et al: "A painful peripheral neuropathy in the rat produced by the chemotherapeutic drug, paclitaxel", Pain, 94:293-304, 2001.

Prado Lima, P.A.S. et al., "Topiramate in treatment-refractory depression" retrieved from STN Database accession No. 1999:61852 XP002179442 Abstract & 11th World Congress of Psychiatry (Aug. 6, 1999), vol. 2,00.126.

Raguraman, et al., "Effects of topiramate in alcohol dependence [2]" Australian and New Zealand Journal of Psychiatry, 2005 Australia, vol. 39, No. 8, 2005, pp. 736-737.

Ramlo-Halsted BA, "The Natural History of Type 2 Diabetes", Primary Care Dec. 1999;26(4):771-89.

Reis et al. Craving decrease with topiramate in outpatient treatment for cocaine dependence: an open label trial, Rev Bras Psiquiatr 2008;30(2):132-5.

Rogaswki et al., Nature Medicine, vol. 10, No. 7, Jul. 2004, pp. 685-692.

Rost et al., The effect of tramadol and other analgesics on the pain . . . , Abstract, Arzneim-Forsch. 1978, vol. 28 (1a0 pp . . . 181-183).

Rouillon, F., Eur. Neuropsychopharmacol 1999, 9 Suppl. 3, S87-S92.

Rygula et al., "Anhedonia and motivational deficits in rats: Impact of chronic social stress", Behavioral Brain Research, 162 (2005) 127-134.

Sanacora, G. et al., "Impairment of GAB Aergic transmission in depression: New Insights from neuroimaging studies", Critical Reviews in Neurobiology, (2000) 14/1 pp. 23-45, XP001029967, whole document.

Scozzafava a et al, "Modulaton of Carbonic Anhydrase Activity and Its Applications in Therapy", Expert Opinion on Therapeutic Patents 2003 United Kingdom, vol. 141 No. 5 (2004) pp. 667-702, XP002331413, ISSN:1354-3776.

Shank et al., "Examination of two independent kinetic assays for determining the inhibition of carbonic anhydrases I and II: Structure-activity comparison of sulfamates and sulfamides" Chemical Biology and Drug Design, vol. 68, No. 2, 2006, pp. 113-119.

Sharma K, McCue P, Dunn Sr. Am J Physiol Renal Physiol. 2003 Jun;284(6):F1138-44.

Silberstein et al., "Migraine & Epilepsy", www.myepilepsy.com, 2002.

Sofuoglu et al., CNS Drugs 2005: 19(1), pp. 13-25.

Stephen, Linda J. et al., "Lamotrigine and topiramate may be a useful combination", The Lancet, vol. 351, No. 9107, pp. 958-959, 1998.

Stephen, Linda J. et al., "Topiramate in Refractory Epilepsy: A Prospective Observational Study", Epilepsia, vol. 41, No. 8, pp. 977-980, 2000.

Stoll et al., Harvard Rev. Psychiatry, Jul./Aug. (1996), vol. 4, No. 2, 77-89.

Storey et al, "Topiramate in Migraine Prevention: A Double Blind, Placebo-Controlled Study", 2001, Headache, 41, pp. 968-975.

Tenovuo, O. "Central Acetylcholinesterase Inhibitors in the Treatment of Chronic Traumatic Brain Injury-Clinical Experience in 111 Patients". Progress in Neuro-Psychopharmacology and Biological Psychiatry 2005 US, vol. 29, No. 1, Jan. 2005, pp. 61067. XP002431412.

The Merck Manual (1987), Merck Sharp & Dohme Research Laboratories, Rahway, NJ XP002144176, pp. 1351-1356.

The Merck Manual, 1999, Merck Research, Whitehouse Station, NJ XP002224345, Diabetes Mellitus, pp. 165-177.

Topiramate retrieved from STN Database Accession No. 1998:2562 XP002179444 Abstract & R&D Focus Drug News, Jul. 27, 1998.

Uhart et al., Addiction Biology, 14, pp. 43-64.

Uys et al., CNS Neurol Disord Drug Targets, 7(5), 2008, pp. 482-91.

Van Amerigen et al. Antiepileptic drugs in the treatment of anxiety disorders: Role in Therapy, Drugs, 2004, 64(19), 2199-2220.

Von Seggern, Randal L., et al, "Efficacy of Topiramate in Migraine Prophylaxis: A Retrospective Chart Analysis" Headache (2002), (42)804-809.

Waugh et al., "Topiramate: As Monotherapy in Newly Diagnosed Epilepsy" CNS Drugs, vol. 17, No. 13, 2003, pp. 985-992.

Wauquier A et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.

WebMD Medical News Epilepsy Drugs Fights Migraine, 2002, www.webmd.com/migraine-headaches/news/20020923/epilepsydrug-fights-migraine.

Wheeler et al., "Topiramate-treated cluster headache", Neurology (Jul. 1999) vol. 53, No. 1 pp. 234-236.

Wheeler S.D., "Antiepileptic Drug therapy in Migraine Headache", Current Treatment Options Neurology, Sep. 2000; 4(5):383-394.

Wheeler, "Significance of migrainouse features in cluster headache", Headache (1998) 38/7 pp. 547-551.

Williams, Jr., J.W., et al., Ann. Intern. Med. 2000, 132, 743-756.

Winhusen et al. Drug and Alcohol Dependence 91 (207) 131-148.

Yang Y. et al., "Neuroprotection by delayed administration of topiratmate in rat model of middle cerebral artery embolization", Brain Research, vol. 804, No. 2, 1998, pp. 169-176, XP000921218.

York, DA et al, "Effects of Topirament on High Fat Diet-Induced Obesity", FASEB journal, Fed. Of America Soc. For Experimental Biology, Bethesda, MD, US., vol. 14, No. 4, Apr. 2000. p. A431, XP000915192.

Young, WB et al, "Topiramate: a case series study in migraine prophylaxis" Cephalalgia (2002), (22)659-663.

Alcaraz et al., Org. Lett., 2004, 6(16), pp. 2705-2708.

Beaudoin et al., J. Org. Chem., 2003, 68, pp. 115-119.

Birch et al., J. Med. Chem., 1999, 42, pp. 3342-3355.

Delgado et al., Tet Lett, 1988, 29(3), pp. 3671-3676.

Estave et al., Tet Lett, 2002, 43, pp. 1019-1021.

Gavernet et al., Bioorg & Med Chem., 2007, 15, pp. 5604-4516.

Hedayatullah et al., Phosphorus and Sulfur, 1985, 25(1), pp. 33-38.

Hirayama et al., Bioorg & Med Chem., 2002, 10, pp. 1509-1523.
Kim et al., Tet Lett, 23(14), pp. 1505-1508.
Kubicki et al., J Mol Struct., 2001, 531(1-3), p. 65-70.
Lee et al., Org. Chem 1990 55(25) pp. 6098-6104.
Muniz et al., Synlett, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., Synlett, 2004, 11, pp. 1901-1904.
Zhong et al., J. Comb. Chem., 2004, 6, pp. 556-563.
Chemische Berichte 1959 92 pp. 509-513.
Notice of Allowance dated Feb. 9, 2010 in U.S. Appl. No. 11/154,443.
Notice of Allowance dated Feb. 23, 2010 in U.S. Appl. No. 11/154,386.
Final Office Action mailed Feb. 25, 2010 in U.S. Appl. No. 11/611,938.
Notice of Allowance dated Jan. 6, 2010 in U.S. Appl. No. 11/611,961.
Final Office Action mailed Jun. 8, 2009 in U.S. Appl. No. 11/612,071.
Final Office Action mailed Oct. 29, 2009 in U.S. Appl. No. 11/612,146.
Office Action mailed Jan. 14, 2010 in U.S. Appl. No. 11/612,202.
Final Office Action mailed Jan. 28, 2010 in U.S. Appl. No. 11/612,249.
Final Office Action mailed Mar. 11, 2010 in U.S. Appl. No. 11/750,600.
Final Office Action mailed Feb. 23, 2010 in U.S. Appl. No. 12/055,433.
Office Action mailed Jan. 29, 2009 in U.S. Appl. No. 11/612,174.
Office Action mailed Nov. 26, 2008 in U.S. Appl. No. 11/612,071.
Office Action mailed May 2, 2008 in U.S. Appl. No. 11/611,961.
Final Office Action mailed Jan. 29, 2009 in U.S. Appl. No. 11/611,961.
Notice of Allowance dated Jun. 2, 2009 in U.S. Appl. No. 11/611,961.
Notice of Allowance dated Apr. 30, 2010 in U.S. Appl. No. 11/611,961.
Office Action mailed May 21, 2008 in U.S. Appl. No. 11/674,021.
Final Office Action mailed Jul. 31, 2009 in U.S. Appl. No. 11/674,021.
Final Office Action mailed Aug. 5, 2008 in U.S. Appl. No. 11/612,146.
Office Action mailed Aug. 17, 2009 in U.S. Appl. No. 11/611,938.
Office Action mailed Mar. 30, 2009 in U.S. Appl. No. 11/612,202.
Office Action mailed Jul. 21, 2009 in U.S. Appl. No. 11/612,249.
Office Action mailed Apr. 29, 2009 in U.S. Appl. No. 11/750,600.
Final Office Action mailed Dec. 16, 2009 in U.S. Appl. No. 11/750,600.
Office Action mailed Jun. 24, 2009 in U.S. Appl. No. 12/055,433.
Notice of Allowance dated Jan. 13, 2010 in U.S. Appl. No. 11/209,122.
Notice of Allowance dated May 25, 2010 in U.S. Appl. No. 11/154,443.
Office Action mailed Oct. 3, 2007 in U.S. Appl. No. 11/154,386.
Notice of Allowance dated Mar. 6, 2009 in U.S. Appl. No. 11/154,386.
Office Action mailed Jul. 9, 2009 in U.S. Appl. No. 11/154,386.
Notice of Allowance dated Sep. 10, 2009 in U.S. Appl. No. 11/154,386.
Office Action mailed Apr. 14, 2008 in U.S. Appl. No. 11/209,122.
Notice of Allowance dated Oct. 30, 2008 in U.S. Appl. No. 11/209,122.
Office Action mailed Mar. 20, 2009 in U.S. Appl. No. 11/209,122.
Notice of Allowance dated Sep. 24, 2009 in U.S. Appl. No. 11/209,122.
Notice of Allowance dated Aug. 12, 2010 in U.S. Appl. No. 11/611,961.
Office Action mailed Jul. 29, 2010 in U.S. Appl. No. 11/612,202.
Office Action mailed Jul. 9, 2010 in U.S. Appl. No. 11/612,222.
Notice of Allowance mailed Jun. 16, 2010 in U.S. Appl. No. 11/674,021.
Notice of Allowance mailed May 28, 2010 in U.S. Appl. No. 11/750,600.
Office Action mailed Jun. 1, 2010 in U.S. Appl. No. 12/488,079.
Keck P et al, "Valproate and carbamazepine in the treatment of panic and post traumatic stress disorders, withdrawals states . . ." J Clin Psychopharm, vol. 12, No. 1, p36S-41S.
Ca 835894-69-4 Sulfamide (1,3-benzodioxol-2-ylmethy), (2005).
CA PLUS 835894-63-8 Sulfamic acid (3,4-dihydro-2H-1benzopyran-2-yl)methylester, (2005).
CA PLUS 835894-65-0 Sulfamide [(3, 4-dihydro-2H-1-benzopyran-2-yl) methyl], (2005).
CA PLUS 835894-67-2 Sulfamic acid (1,3-benzodioxol-2-ylmethyl ester), 2005.
Migraine: Treatments and drugs, by Mayo Clinic Staff, http://www.mayoclinic.com/health/migraineheadache/DS00120/DSECTION=treatments-and-drugs.
Uhart et al., Addiction Biology, 14, pp. 43-64, (2008).
Winhusen et al. Drug and Alcohol Dependence 91 131-148, (2007).
Kim et al., Tet Lett, 23 (14), pp. 1505-1508, (1982).
Agrawal et al., Bioorganic and Medicinal Chemistry, 11(2003), pp. 5353-5362.
Behl et al., Endocrinology, vol. 138, No. 1, pp. 101-106, (1997).
Casini et al., Bioorganic and Medicinal Chemistry Letters, 13(2003), pp. 841-845.
Cleeves et al., "Trazodone is ineffective in essential tremor", J. Neurol Nerusurg Psychiatry, 1990, 53:268-269.
Coyle et al., Science, vol. 262, Issue 5134, pp. 689-695 (1993).
Desagher et al., The Journal of Neuroscience, 1996, 16(8), pp. 2553-2562.
Koller et al., "Essential Tremor Variants: Effect of Treatment", abstract, Clinical Pharmacology, 1987.
Merck Manuals Online Medical Library, www.merck.com, 2007.
New England Journal of Medicine, vol. 342:505-507, 2001.
Nickel et al., Journal of Affective Disorders, vol. 87(2-3), 2005, pp. 243-252.
Pasorekova et al., Journal of Enzyme Inhibition and Medicinal Chemistry, Jun. 2004, vol. 19(3), pp. 199-229.
Robinson et al. "Pregablin not Effective for Essential Tremor", www.medpagetoday.com, 2009.
Rogawski et al., Nature Reviews Neuroscience, vol. 5 (1), 2004, pp. 553-564.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al. Exp. Opin. Ther. Patents, 12(2), pp. 217-242 (2002).
Supuran et al., Exp. Opin. Ther. Patents, (2000), 10(5), pp. 575-600.
Supuran et al., Medicinal Research Reviews, vol. 23, No. 2, pp. 146-189, 2003.
Tabner et al., The Journal of Biological Chemistry, vol. 280, No. 43, pp. 35789-35792, Oct. 28, 2005.
Taylor et al., Science, vol. 296, pp. 1991-1995 (2002).
Thakur at al., Bioorganic and Medicinal Chemistry, 12(2004), pp. 789-793.
Office Action mailed Mar. 26, 2008 in U.S. Appl. No. 11/154,443.
Notice of Allowance mailed Dec. 31, 2008 U.S. Appl. No. 11/154,443.
Notice of Allowance dated Jun. 8, 2009 in U.S. Appl. No. 11/154,443.
Notice of Allowance dated Oct. 9, 2009 in U.S. Appl. No. 11/154,443.
Notice of Allowance dated Sep. 20, 2010 in U.S. Appl. No. 11/154,443.
Notice of Allowance dated Jan. 25, 2011 in U.S. Appl. No. 11/154,443.
Notice of Allowance dated Oct. 22, 2010 in U.S. Appl. No. 11/154,386.
Notice of Allowance dated Jan. 11, 2011 in U.S. Appl. No. 11/209,122.
Notice of Allowance dated Nov. 30, 2010 in U.S. Appl. No. 11/611,961.
Office Action mailed Nov. 15, 2010 in U.S. Appl. No. 11/612,202.
Office Action mailed Oct. 15, 2010 in U.S. Appl. No. 11/612,249.
Notice of Allowance mailed Dec. 15, 2010 in U.S. Appl. No. 11/674,021.

Notice of Allowance mailed Dec. 15, 2010 in U.S. Appl. No. 11/750,600.
Office Action mailed Sep. 22, 2010 in U.S. Appl. No. 12/055,433.
Office Action mailed Nov. 15, 2010 in U.S. Appl. No. 12/055,924.
Notice of Allowance mailed Dec. 14, 2010 in U.S. Appl. No. 12/488,079.
Handley and Mithani, Naunyn. Schmied. Arch. Pharmacol., 327, 1-5, 1984.
Aron et al., Neuropharmacology, 10, 459-469, 1971.
Meert et al., Pharmacol. Biochem. Behav.; 2005, 80(2), pp. 309-326.
MacDonald et al., CNS Drugs, 2002, 16(8): 549-562.
Walden et al., Neuropsychobiology, 1998,38: 181-84.
Supuran et al., Exp. Opin. Ther. Patents, 2002, 12(2), pp. 217-242.
Notice of Allowance dated May 4, 2011 in U.S. Appl. No. 11/154,443.
Notice of Allowance dated Mar. 14, 2011 in U.S. Appl. No. 11/611,961.
Notice of Allowance dated Mar. 4, 2011 in U.S. Appl. No. 11/612,202.
Office Action mailed Apr. 12, 2011 in U.S. Appl. No. 11/612,222.
Office Action mailed Apr. 22, 2011 in U.S. Appl. No. 11/612,249.
Office Action mailed Jun. 8, 2011 in U.S. Appl. No. 12/055,433.
Office Action mailed May 26, 2011 in U.S. Appl. No. 12/055,695.
Notice of Allowance dated Jun. 1, 2011 in U.S. Appl. No. 11/209,122.
Bernando, L., Prevention of epilepsy after head trauma: do we need drugs or a new approach?, 2003, Epilepsia, 44, (Suppl. 10), 27-33.
Byrn et al., Pharmaceutical Research, Kluwer Academic Publishers, New York, NY, US, vol. 12, No. 7, 1995, pp. 945-954.
D'Ambrosio et al., Curr. Opin. Neurol. Dec. 2004; 17(6): 731-735.
Jones et al. "Screening for Major Depression in Epilepsy with Common Self-Report Depression Inventories", Epilepsia, May 2005; 46(5):731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Notice of Allowance dated Aug. 12, 2011 in U.S. Appl. No. 11/154,443.
Notice of Allowance dated Jul. 18, 2011 in U.S. Appl. No. 11/611,961.
Office Action mailed Jul. 11, 2011 in U.S. Appl. No. 12/431,141.
Notice of Allowance dated Sep. 19, 2011 in U.S. Appl. No. 11/612,202.
Notice of Allowance dated Aug. 22, 2011 in U.S. Appl. No. 11/674,021.
Office Action/Interview Summary dated Sep. 1, 2011 in U.S. Appl. No. 11/750,600.
Notice of Allowance dated Sep. 12, 2011 in U.S. Appl. No. 11/750,600.
Office Action mailed Jul. 15, 2011 in U.S. Appl. No. 12/055,695.
Notice of Allowance mailed Apr. 12, 2011 in U.S. Appl. No. 12/055,924.
Notice of Allowance dated Jun. 21, 2011 in U.S. Appl. No. 12/488,079.
Office Action mailed Jul. 8, 2011 in U.S. Appl. No. 12/502,472.
Harwood, AJ, Molecular Psychiatry (2005) 10,117-126.
Goodman and Gilman's The Pharmacological Basis of Therapeutics, Eleventh Edition, McGraw Hill, Hypnotics and Sedatives, Chapter 16, pp. 401-427 (2006).
Goodman and Gilman's The Pharmacological Basis of Therapeutics, Eleventh Edition, McGraw Hill, Hypnotics and Sedatives, Chapter 17, pp. 429-459 (2006).
Goodman and Gilman's The Pharmacological Basis of Therapeutics, Eleventh Edition, McGraw Hill, Hypnotics and Sedatives, Chapter 19, pp. 429-459 (2006).
Notice of Allowance dated Oct. 18, 2011 in U.S. Appl. No. 11/209,122.
Notice of Allowance dated Oct. 26, 2011 in U.S. Appl. No. 11/611,961.
Notice of Allowance dated Oct. 11, 2011 in U.S. Appl. No. 11/612,071
Final Office Action mailed Dec. 15, 2011 in U.S. Appl. No. 12/431,141.
Office Action mailed Oct. 4, 2011 in U.S. Appl. No. 10/612,222.
Office Action mailed Oct. 6, 2011 in U.S. Appl. No. 10/612,249.
Notice of Allowance dated Dec. 22, 2011 in U.S. Appl. No. 11/750,600.
Office Action mailed Dec. 22, 2011 in US U.S. Appl. No. 12/055,433.
Office Action mailed Nov. 21, 2011 in U.S. Appl. No. 12/055,695.
Office Action mailed Oct. 6, 2011 in U.S. Appl. No. 12/349,184.
Notice of Allowance dated Nov. 1, 2011 in U.S. Appl. No. 12/488,079.
Notice of Allowance mailed Nov. 28, 2011 in U.S. Appl. No. 12/502,472.
O'Donnell et al., Chapter 15, "Drug Therapy of Depression and Anxiety Disorders", Goodman & Gilman's the Pharmacological Basis of Therapeutics, 12th Edition, 2011, pp. 397-415.
McNamara, J., Chapter 21, "Pharmacotherapy of the Epilepsies", Goodman & Gilman's The Pharmacological Basis of Therapeutics, 12th Edition, 2011, pp. 583-607.
Brodie, M.S.; Pesold, C; Appel, S.B. Alcohol Clin Exp Res 1999,23,1848-1852.
Sullivan, P., Epilepsy & Behavior 7 (2005) S12—S17.
Wise RA, Drug Alcohol Depend, 1998, 51, 13-22.
Wise RA, NIDE Res Mono, 1984,50,15-33.
Notice of Allowance dated Mar. 20, 2012 in U.S. Appl. No. 11/209,122.
Notice of Allowance dated Feb. 6, 2012 in U.S. Appl. No. 11/611,961.
Notice of Allowance mailed Mar. 9, 2012 in U.S. Appl. No. 11/612,071.
Interview Summary dated Mar. 26, 2012 in U.S. Appl. No. 12/431,141.
Notice of Allowance mailed Jan. 4, 2012 in U.S. Appl. No. 11/612,202.
Notice of Allowance mailed Apr. 16, 2012 in U.S. Appl. No. 11/612,202.
Office Action dated Mar. 30, 2012 in U.S. Appl. No. 11/750,600.
Interview Summary dated Apr. 4, 2012 in U.S. Appl. No. 12/055,433.
Notice of Allowance dated Mar. 1, 2012 in U.S. Appl. No. 12/488,079.
Notice of Allowance dated Mar. 28, 1012 in U.S. Appl. No. 12/502,472.

* cited by examiner

PROCESS FOR PREPARATION OF SULFAMIDE DERIVATIVES

CROSS REFERENCE TO RELATED APPLICATIONS

This application claims the benefit of U.S. Provisional Application 60/683,151, filed on May 20, 2005, which is incorporated by reference herein in its entirety.

FIELD OF THE INVENTION

The present invention is directed to a novel process for the preparation of sulfonylimine and sulfamide derivatives.

SUMMARY OF THE INVENTION

The present invention is directed to a process for the preparation of a sulfonylimine derivative, comprising reacting an aldehyde with a substituted or unsubstituted sulfamide, in a suitable organic solvent, in the presence of an acid or TMSCI, to yield the corresponding sulfonylimine derivative.

The present invention is further directed to a process for the preparation of sulfamide derivative or a pharmaceutically acceptable salt thereof, comprising reacting an aldehyde with a substituted or unsubstituted sulfamide, in a suitable organic solvent, in the presence of an acid or TMSCI, to yield the corresponding sulfonylimine;

reducing or hydrogenating the sulfonylimine, in a suitable organic solvent, to yield the corresponding sulfamide derivative.

In an embodiment, the present invention is directed to a process for the preparation of compounds of formula (I)

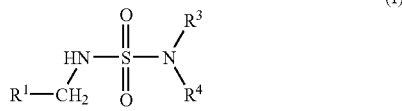

wherein $R^1$ is selected from the group consisting of alkyl, carbocyclyl, aryl, heteroaryl and heterocycloalkyl; wherein the alkyl, carbocyclyl, aryl, heteroaryl and heterocycloalkyl is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

$R^3$ and $R^4$ are each independently selected from the group consisting of alkyl, carbocyclyl, aryl, heteroaryl and heterocycloalkyl; wherein the alkyl, carbocyclyl, aryl, heteroaryl and heterocycloalkyl is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

alternatively, $R^3$ and $R^4$ are taken together with the nitrogen atom to which they are bound to form a monocyclic or bicyclic, saturated, partially unsaturated, partially aromatic or aromatic ring structure; wherein the ring structure is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

or a pharmaceutically acceptable salt thereof;

comprising

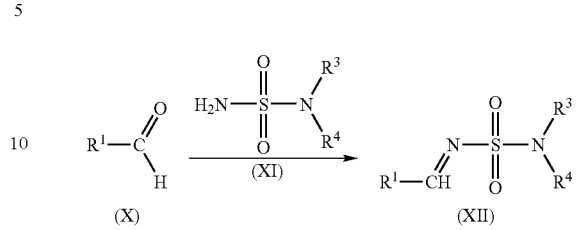

reacting a compound of formula (X) with a compound of formula (XI), in the presence of an acid or TMSCI, in a suitable organic solvent, to yield the corresponding compound of formula (XII);

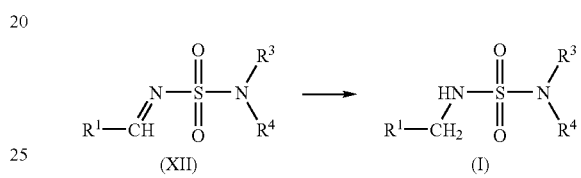

reducing or hydrogenating the compound of formula (XII), in a suitable organic solvent, to yield the corresponding compound of formula (I).

In another embodiment of the present invention is a process for the preparation of a compound of formula (XII)

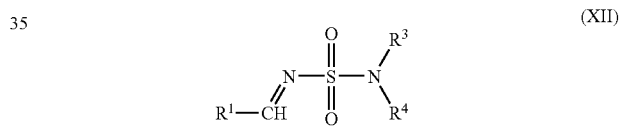

wherein $R^1$ is selected from the group consisting of alkyl, carbocyclyl, aryl, heteroaryl and heterocycloalkyl; wherein the alkyl, carbocyclyl, aryl, heteroaryl and heterocycloalkyl is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

$R^3$ and $R^4$ are each independently selected from the group consisting of alkyl, carbocyclyl, aryl, heteroaryl and heterocycloalkyl; wherein the alkyl, carbocyclyl, aryl, heteroaryl and heterocycloalkyl is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

alternatively, $R^3$ and $R^4$ are taken together with the nitrogen atom to which they are bound to form a monocyclic or bicyclic, saturated, partially unsaturated, partially aromatic or aromatic ring structure; wherein the ring structure is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

or a pharmaceutically acceptable salt thereof; comprising

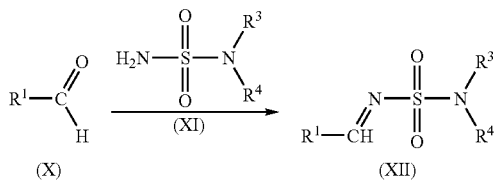

reacting a compound of formula (X) with a compound of formula (XI), in the presence of an acid or TMSCl, in a suitable organic solvent, to yield the corresponding the compound of formula (XII).

The present invention is further directed to compounds of formula (XII), as herein defined.

The present invention is further directed to a product prepared according to any of the processes described herein.

DETAILED DESCRIPTION OF THE INVENTION

The present invention is directed to a process for the preparation of sulfonylimine derivatives. The present invention is further directed to a process for the preparation of sulfamide derivatives and pharmaceutically acceptable salts thereof. The sulfonylimine derivatives are useful, for example, as intermediates in the synthesis of pharmaceutical agents such as the sulfamide derivatives described herein. The sulfamide derivatives, for example, the compounds as listed in Table 1 herein, are useful for the treatment of epilepsy.

In an embodiment, the present invention is directed to a process for the preparation of sulfamide derivatives of formula (I)

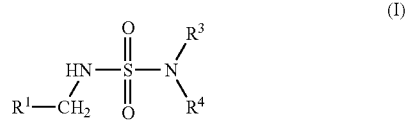

wherein $R^1$, $R^3$ and $R^4$ are as herein defined.

In an embodiment of the present invention $R^1$ is unsubstituted alkyl. In another embodiment of the present invention $R^1$ is an aromatic ring structure. In another embodiment of the present invention, $R^1$ is a 5-6 membered aromatic ring structure. In another embodiment of the present invention, $R^1$ is selected from the group consisting of aryl and heteroaryl, wherein the aryl or heteroaryl is optionally substituted.

In an embodiment of the present invention $R^3$ and $R^4$ are each independently selected from hydrogen or $C_{1-4}$alkyl. In another embodiment of the present invention, $R^3$ and R4 are each independently selected from hydrogen or methyl. In another embodiment of the present invention, $R^3$ and $R^4$ are each hydrogen.

In an embodiment of the present invention, $R^3$ and $R^4$ are taken together to form a 5 to 7 membered, substituted or unsubstituted ring structure. Preferably, the 5 to 7 membered ring structure is saturated or aromatic.

Additional embodiments of the present invention, include those wherein the substituents selected for one or more of the variables defined herein (i.e. $R^1$, $R^3$, and $R^4$) are independently selected to be any individual substituent or any subset of substituents selected from the complete list as defined herein.

Compounds of formula (I) may be prepared according to the process outlined in detail in Scheme 1 below.

Scheme 1

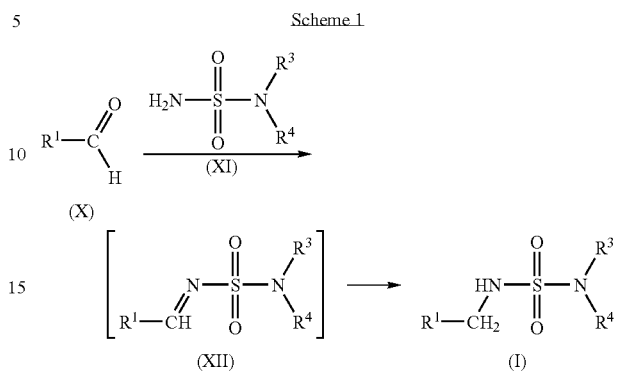

Accordingly, a suitably substituted compound of formula (X), a known compound or compound prepared by known methods, is reacted with a suitably substituted compound of formula (XI), a known compound or compound prepared by known methods;

in the presence an acid such as p-toluene sulfonic, TFA, acetic acid, HCl (preferably anhydrous HCl), sulfamic acid, and the like, preferably in the presence of p-toluene sulfonic acid or sulfamic acid; or in the presence of TMSCl;

wherein acid is present in present in at least a catalytic amount, preferably in amount in the range of from about a catalytic amount to about 10 mole % relative to the aldehyde (for example, compound of formula (X)), more preferably, in about a catalytic amount;

wherein the TMSCl is present in at least a catalytic amount, preferably in amount in the range of from about a catalytic amount to about 2 equivalents, more preferably, at about 1 equivalent;

in a suitable organic solvent such as THF, acetonitrile, methanol, ethanol, propanol, DMF, and the like, preferably in a polar organic solvent, more preferably, in a polar organic solvent which dissolves the compound of formula (XI) at least partially, more preferably still, in ethanol or THF;

preferably, at a temperature greater than or equal to about 20° C., more preferably, at a temperature in the range of from about 40° C. to about 60° C.;

to yield the corresponding compound of formula (XII), wherein the compound of formula (XII) is preferably not isolated.

One skilled in the art will recognize that the acid is preferably strong enough to activate the carbonyl portion of the aldehyde of compound of formula (X), thereby facilitating the nucleophilic reaction between the aldehyde and the substituted or unsubstituted sulfamide. Suitable examples of such acids include, but are not limited to, p-toluene sulfonic, TFA, acetic acid, HCl (preferably anhydrous HCl), sulfamic acid, and the like.

The compound of formula (XII) is reacted with a reducing agent such as $NaBH_4$, $LiBH_4$, $Na(OAc)_3BH$, LAH, and the like; in a suitable organic solvent such as THF, acetonitrile, methanol, ethanol, propanol, DMF, dichloroethane, and the like, preferably in a polar organic solvent, more preferably, in the same solvent used in the previous reaction step; to yield the corresponding compound of formula (I). One skilled in the art will recognize that the organic solvent is selected to be compatible with the selected reducing agent. For example, one skilled in the art will recognize that the suitable organic solvent when using LAH would be an ether such as THF, diethyl ether, dioxane, dimethoxyethane, and the like; but would not be methanol, ethanol, propanol acetonitrile, DMF, and the like.

Alternatively, the compound of formula (XII) is hydrogenated by reacting with hydrogen gas or a source of hydrogen; in the presence of a catalyst such as Pd on carbon, rhodium on alumina, $PdCl_2$, and the like; in a suitable organic solvent which is not reactive under the hydrogenation conditions, such as THF, methanol, ethanol, propanol, DMF, and the like, preferably in a polar organic solvent such as an alcohol, more preferably, in the same solvent used in the previous reaction step; to yield the corresponding compound of formula (I).

One skilled in the art will recognize that wherein a substituent on the aldehyde (e.g. a substituent on the compound of formula (X), for example an aldehyde, carboxylic acid, amino, alkylamino, and the like) is reactive to the sulfamide, said substituent is preferably protected prior to reacting the aldehyde with the sulfamide and then de-protected following the reduction/hydrogenation, to yield the corresponding sulfamide derivative.

One skilled in the art will further recognize that in reacting the compound of formula (XII) to yield the corresponding compound of formula (I), the reducing or hydrogenating conditions are selected to avoid reactions with any substituent groups and therefore to provide the desired product.

One skilled in the art will further recognize that the sulfamide comprises two amine groups which may have the same or different reactivity relative to the aldehyde. One skilled in the art will further recognize that by protecting one of the two amines on the sulfamide, the reaction can be directed to yield coupling between the unprotected amine portion of the sulfamide and the aldehyde. The protected amine portion of the sulfamide is then, optionally, de-protected to yield the corresponding sulfamide derivative.

As used herein, "halogen" shall mean chlorine, bromine, fluorine and iodine.

As used herein, the term "alkyl" whether used alone or as part of a substituent group, include straight and branched chains, preferably a straight or branched chain comprising one to ten carbon atoms. For example, alkyl radicals include methyl, ethyl, propyl, isopropyl, butyl, isobutyl, sec-butyl, t-butyl, pentyl and the like. Unless otherwise noted, "$C_{1-4}$alkyl" means a carbon chain composition of 1-4 carbon atoms.

As used herein, unless otherwise noted, "aryl" shall refer to unsubstituted carbocylic aromatic groups such as phenyl, naphthyl, fluorenyl, and the like. Preferably, the aryl group is phenyl or naphthyl, more preferably, phenyl.

As used herein, unless otherwise noted, the term "cycloalkyl" shall mean any stable monocyclic, bicyclic, polycyclic or bridged, saturated ring system, for example cyclopropyl, cyclobutyl, cyclopentyl, cyclohexyl, cycloheptyl, cyclooctyl, norbornyl, decahydronapthyl, and the like.

As used herein, unless otherwise noted, the term "carbocyclyl" shall mean any stable monocyclic, bicyclic, polycyclic or bridged ring structure, wherein the ring structure comprises is saturated, partially unsaturated or partially aromatic. Suitable examples include, tetrahydronaphthyl, cyclohexenyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S; or any polycyclic ring structure containing at least one heteroatom selected from the group consisting of O, N and S, optionally containing one or more, preferably one to three, additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

When a particular group is "substituted" (e.g., alkyl, phenyl, aryl, heteroalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, the term "sulfonylimine" is intended to denote a derivative which comprises the following chemical group

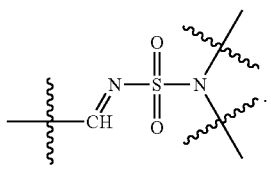

Under standard nomenclature used throughout this disclosure, the terminal portion of the designated side chain is described first, followed by the adjacent functionality toward the point of attachment. Thus, for example, a "phenylC$_1$-C$_6$alkyl-amino-carbonyl-C$_1$-C$_6$alkyl-" substituent refers to a group of the formula

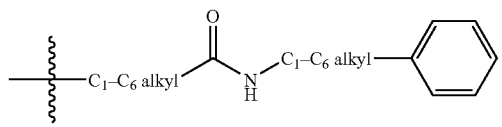

Abbreviations used in the specification, particularly the Schemes and Examples, are as follows:
DCM=Dichloromethane
DMF=N,N-Dimethylformamide
HPLC=High pressure liquid chromatography
LAH=Lithium aluminum hydride
Na(OAc)$_3$BH=Sodium triacetoxyborohydride
NMR=Nuclear Magnetic Resonance
THF=Tetrahydrofuran
TFA=Trifluoroacteic acid
TLC=Thin Layer Chromatography
TMSCl=Chlorotrimethylsilane Representative sulfamide compounds which were prepared according to the process of the present invention, as described in more detail in the Examples which follow, are as listed in Table 1, below.

TABLE 1

Representative Compounds of Formula (I)

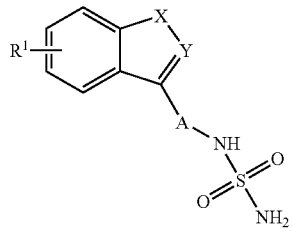

| ID No. | R$^1$ | —X—Y— | A |
|---|---|---|---|
| 1 | H | —S—CH— | —CH$_2$— |
| 7 | H | —N(CH$_3$)—CH— | —CH$_2$— |
| 13 | H | —O—C(CH$_3$) | —CH$_2$— |
| 15 | 5-Br | —S—CH— | —CH$_2$— |
| 17 | 4-Br | —S—CH— | —CH$_2$— |
| 18 | 7-F | —S—CH— | —CH$_2$— |

Additional compounds prepared according to the procedures as described in the Schemes above and the Examples which follow include those listed in Table 2 below.

TABLE 2

| ID No. | Structure |
|---|---|
| 25 | 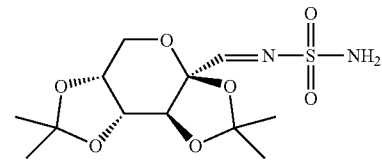 |
| 26 | 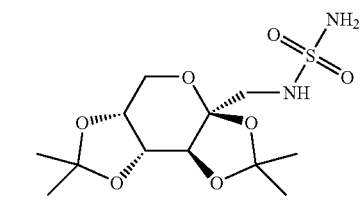 |
| 30 | 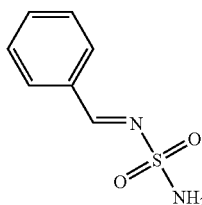 |

TABLE 2-continued

| ID No. | Structure |
|---|---|
| 31 | H₂N-S(=O)(=O)-N(piperidine)-phenyl |
| 32 | benzo[b]thiophen-3-ylmethyl-NH-S(=O)(=O)-N(piperidine)-phenyl |

The following Examples are set forth to aid in the understanding of the invention, and are not intended and should not be construed to limit in any way the invention set forth in the claims which follow thereafter.

Example 1

N-(benzo[b]thien-3-ylmethyl)-sulfamide (Compound #1)

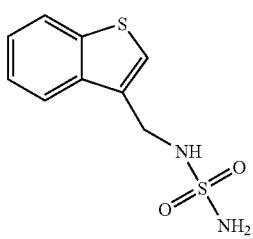

Thianaphthene-3-carboxaldehyde (1.62 g, 10.0 mmol) was dissolved in anhydrous ethanol (50 mL). Sulfamide (4.0 g, 42 mmol) was added and the mixture was heated to reflux for 16 hours. The mixture was cooled to room temperature. Sodium borohydride (0.416 g, 11.0 mmol) was added and the mixture was stirred at room temperature for three hours. The reaction was diluted with water (50 mL) and extracted with chloroform (3×75 mL). The extracts were concentrated and chromatographed (5% methanol in DCM) to yield the title compound as a white solid.

$^1$H NMR (DMSO-d$_6$): δ 7.98 (1H, dd, J=6.5, 2.3 Hz), 7.92 (1H, dd, J=6.6, 2.4 Hz), 7.62 (1H, s), 7.36-7.45 (2H, m), 7.08 (1H, t, J=6.3 Hz), 6.72 (2H, s), 4.31 (2H, d, J=6.3 Hz).

Example 2

N-[(1-methyl-1H-indol-3-yl)methyl]-sulfamide (Compound #7)

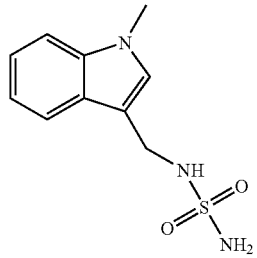

N-Methylindole-3-carboxaldehyde (1.66 g, 10.4 mmol) was dissolved in anhydrous ethanol (50 mL). Sulfamide (4.5 g, 47 mmol) was added and the mixture was heated to reflux for 16 hours. Additional sulfamide (1.0 g, 10.4 mmol) was added and the mixture was heated to reflux for 24 hours. The mixture was cooled to room temperature. Sodium borohydride (0.722 g, 12.5 mmol) was added and the mixture was stirred at room temperature for one hour. The reaction was diluted with water (50 mL) and extracted with DCM (3×75 mL). The extracts were concentrated and about 1 mL of methanol was added to create a slurry which was filtered to yield the title compound as a white powder.

$^1$H NMR (CD$_3$OD): δ 7.67 (1H, d, J=5.9 Hz), 7.32 (1H, d, J=6.2 Hz), 7.14-7.19 (2H, m), 7.06 (1H, dt, J=7.7, 0.7 Hz), 4.36 (2H, s), 3.75 (3H, s)

MS (M-H)⁻ 237.6.

Example 3

N-[(2-methyl-3-benzofuranyl)methyl]-sulfamide (Compound #13)

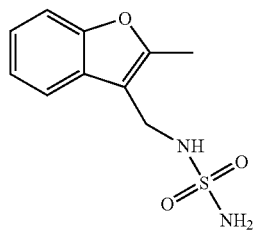

2-Methylbenzofuran-3-carbaldehyde (0.51 g, 3.18 mmol) was dissolved in anhydrous ethanol (25 mL). Sulfamide (1.5 g, 16 mmol) was added and the mixture was heated to reflux for 4 days. The mixture was cooled to room temperature. Sodium borohydride (0.132 g, 3.50 mmol) was added and the mixture was stirred at room temperature for 24 hours. The reaction was diluted with water (100 mL) and extracted with DCM (3×75 mL). The extracts were concentrated and suspended in a minimal amount of DCM and filtered to yield the title compound as a white solid.

¹H NMR (DMSO-d₆): δ 7.65 (1H, dd, J=6.4, 2.6 Hz), 7.43-7.47 (1H, m), 7.19-7.23 (2H, m), 6.87 (1H, t, J=6.2 Hz), 6.68 (2H, s), 4.11 (2H, d, J=6.2 Hz), 2.42 (3H, s).

Example 4

N-[(5-bromobenzo[b]thien-3-yl)methyl]-sulfamide
(Compound #15)

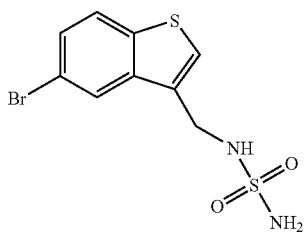

5-Bromobenzothiophene (1.60 g, 7.51 mmol) and dichloromethyl methyl ether (1.29 g, 11.3 mmol) were dissolved in anhydrous 1,2-dichloroethane (75 mL). Titanium tetrachloride (2.14 g, 11.3 mmol) was added, turning the solution dark. After one hour at room temperature, the reaction was poured into a mixture of saturated aqueous NaHCO₃ and ice. The mixture was stirred for about 30 minutes and then was extracted with DCM (2×100 mL). The extracts were concentrated and chromatographed (0 to 5% ethyl acetate in hexane) to yield 5-bromo-benzo[b]thiophene-3-carbaldehyde (1.32 g). The 5-bromobenzothiophene-3-carboxaldehyde (1.20 g, 4.98 mmol) and sulfamide (4.0 g, 42 mmol) were combined in anhydrous ethanol (25 mL) and heated to reflux for three days. The reaction was cooled to room temperature and sodium borohydride (0.207 g, 5.47 mmol) was added. After five hours, water (50 ml) was added and the solution was extracted with chloroform (3×50 mL). The extracts were concentrated, suspended in a minimal amount of DCM, and filtered to provide the title compound as a yellow solid.

¹H NMR (DMSO-d₆): δ 8.12 (1H, d, J=1.8 Hz), 7.97 (1H, d, J=8.6), 7.71 (1H, s), 7.52 (1H, dd, J=8.6, 1.9 Hz), 7.12 (1H, t, J=6.3 Hz), 6.72 (2H, s), 4.28 (2H, d, J=6.2 Hz).

Example 5

N-[(4-bromobenzo[b]thien-3-yl)methyl]-sulfamide
(Compound #17)

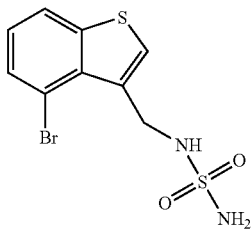

4-Bromobenzothiophene (1.80 g, 8.45 mmol) and dichloromethyl methyl ether (1.46 g, 12.7 mmol) were dissolved in anhydrous DCM (100 mL). Titanium tetrachloride (2.40 g, 12.7 mmol) was added, turning the solution dark. After 30 minutes at room temperature, the reaction was poured into a mixture of saturated aqueous NaHCO₃ and ice. The mixture was stirred for about 30 minutes and then was extracted with DCM (2×150 mL). The extracts were concentrated and chromatographed (0 to 15% ethyl acetate in hexane) to yield 4-bromobenzothiophene-3-carboxaldehyde (0.910 g). The 4-bromobenzothiophene-3-carboxaldehyde (0.910 g, 3.77 mmol) and sulfamide (3.0 g, 31 mmol) were combined in anhydrous ethanol (25 mL) and heated to reflux for three days. The reaction was cooled to room temperature and sodium borohydride (0.157 g, 4.15 mmol) was added. After five hours, water (50 ml) was added and the solution was extracted with chloroform (3×50 mL). The extracts were concentrated, suspended in a minimal amount of DCM, and filtered to yield the title compound as a yellow solid.

¹H NMR (DMSO-d₆): δ 8.05 (1H, dd, J=8.1, 0.8 Hz), 7.78 (1H, s), 7.64 (1H, dd, J=7.6, 0.8 Hz), 7.27 (1H, t, J=7.9 Hz), 7.13 (1H, t, J=6.3 Hz), 6.72 (2H, br s), 4.65 (2H, d, J=5.3 Hz).

Example 6

N-[(7-fluorobenzo[b]thien-3-yl)methyl]-sulfamide
(Compound #18)

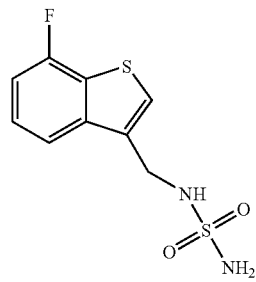

2-Fluorothiophenol (4.14 g, 32.6 mmol) was dissolved in anhydrous THF (100 mL). Potassium tert-butoxide (1.0 M in THF, 35.8 mL) was added and the suspension was stirred at room temperature for 15 minutes. 2-Chloroacetaldehyde dimethyl acetal was added and the mixture was stirred for 3 days. Water (100 mL) was added and the solution was extracted with diethyl ether (3×100 mL). The extracts were concentrated to a yellow oil and chromatographed (5 to 20% ethyl acetate in hexane) to yield 1-(2,2-dimethoxy-ethylsulfanyl)-2-fluoro-benzene (6.42 g) as a colorless oil. Chlorobenzene (25 mL) was heated to reflux and polyphosphoric acid (1 mL) was added. The 1-(2,2-dimethoxy-ethylsulfanyl)-2-fluoro-benzene was then added slowly turning the solution dark. After 3 hours of heating, the reaction was cooled to room temperature and diluted with water (50 mL). The solution was extracted with benzene (2×50 mL). The extracts were concentrated and chromatographed (0 to 15% ethyl acetate in hexane) to yield 7-fluorobenzothiophenyl (0.77 g). The 7-fluorobenzothiophenyl (0.77 g, 5.1 mmol) and dichloromethyl methyl ether (0.872 g, 7.6 mmol) were dissolved in anhydrous DCM (25 mL). Titanium tetrachloride (1.0 M in DCM, 7.6 mL, 7.6 mmol) was added, turning the solution dark. After 30 minutes at room temperature, the reaction was poured into a mixture of saturated aqueous NaHCO₃ and ice. The mixture was stirred for about 30 minutes and then was extracted with DCM (2×50 mL). The extracts were concentrated and chromatographed (0 to 15% ethyl acetate in hexane) to yield 7-fluorobenzothiophene-3-carboxaldehyde (0.642 g). The 7-fluorobenzothiophene-3-carboxaldehyde (0.642 g, 3.77 mmol) and sulfamide (1.7 g, 18 mmol) were combined in anhydrous ethanol (20 mL) and heated to reflux for three days. The reaction was cooled to room temperature and sodium borohydride (0.148 g, 3.92 mmol) was added. After two hours, water (25 ml) was added and the solution was extracted with chloroform (3×25 mL). The extracts were concentrated, suspended in a minimal amount of DCM, and filtered to yield the title compound as a yellow solid.

$^1$H NMR (DMSO-$d_6$): δ 7.78 (1H, d, J=8.0 Hz), 7.43-7.50 (1H, m), 7.27 (1H, dd, J=10.3, 7.9 Hz), 7.14 (1H, t, J=6.4 Hz), 6.74 (2H, br s), 4.31 (2H, d, J=6.4 Hz).

Example 7

1-[(Aminosulfonyl)imino]-1-deoxy-2,3:4,5-bis-O-(isopropylidene)-D-fructopyranose (Compound #25)

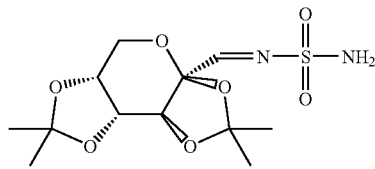

2,3:4,5-bis-O-(isopropylidene)-D-fructopyranose aldehyde, a compound of the formula

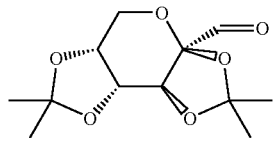

(1.0 g, 3.9 mmol) and sulfamide (0.7 g, 8 mmol) were heated to 100° C. in toluene (20 mL) for 12 hours. The reaction mixture was then cooled to room temperature. The resulting solid was filtered and crystallized from methanol (20 mL). The solid was filtered and dried to yield the title compound as a brown solid.

$^1$H NMR (DMSO-$d_6$): δ 6.85 (1H, s), 6.47 (1H, s), 7.62 (1H, s), 4.92 (1H, s), 4.57 (1H, dd, J=8.5 Hz, J=2.4 Hz), 4.30 (1H, d, J=2.4 Hz), 4.25 (1H, d, J=8.8 Hz), 3.72 (2H, q, J=13.0 Hz, J=7.9 Hz), 1.48 (3H, s), 1.41 (3H, s), 1.37 (3H, s), 1.29 (3H, s).

Example 8

1-[(Aminosulfonyl)amino]-1-deoxy-2,3:4,5-bis-O-(isopropylidene)-D-fructopyranose (Compound #26)

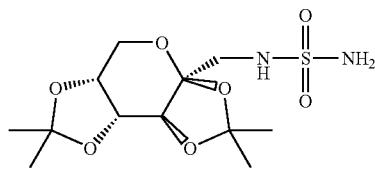

1-[(Aminosulfonyl)imino]-1-deoxy-2,3:4,5-bis-O-(isopropylidene)-D-fructopyranose, prepared as in Example 7 above, (0.2 g, 0.6 mmol) was dissolved in anhydrous ethanol (1 mL). Sodium borohydride (0.05 g, 2.0 mmol) was then added and the reaction mixture was stirred at room temperature for one hour. The reaction was quenched by addition of 1N HCl, the product extracted with ethyl acetate (10 mL) and concentrated to yield the title compound.

$^1$H NMR (CDCL$_3$): δ 5.13-5.01 (1H, m), 4.88-4.75 (2H, m), 4.61 (1H, d, J=7.2 Hz), 4.31-4.21 (2H, m), 3.84, (2H, q, J=19.7 Hz, J=14.5 Hz), 3.58-3.35 (2H, m), 1.66 (3H, s), 1.55 (3H, s), 1.42 (3H, s), 1.37 (3H, s).

Example 9

N-Aminosulfonyl Benzylideneamine (Compound #30)

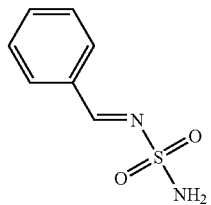

Benzaldehyde (5 g, 4 mmol) and sulfamide (9.06 g, 94 mmol) were dissolved in anhydrous ethanol (100 mL). The reaction mixture was heated to reflux for 2 hours then cooled to room temperature. The resulting solid was filtered and dried to yield the title compound.

$^1$H NMR (DMSO-$d_6$): δ 8.95 (1H, s), 8.02 (2H, d, J=7.9 Hz), 7.71 (1H, t, J=6.9 Hz), 7.61, (2H, dd, J=7.9 Hz, J=6.9 Hz), 7.44 (2H, s).

Example 10

N-(benzo[b]thien-3-ylmethyl)-sulfamide (Compound #1)

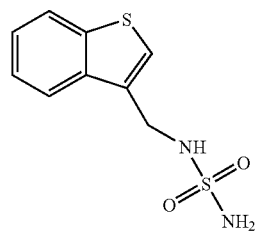

Thianaphthene-3-carboxaldehyde (5 g, 30.8 mmol) was dissolved in anhydrous ethanol (50 mL). Sulfamide (12.22 g, 123.30 mmoles) and sulfamic acid (0.29 g, 3.08 mmoles) were added and the reaction mixture heated to 45° C. for 18 h. The reaction mixture was then cooled to room temperature. Sodium borohydride (1.2 g, 30.8 mmol) was added and the reaction mixture was stirred for 1 hour. 1N HCl (30 mL, 30 mmol) was added and the reaction mixture was filtered through Celite. The filtered solution was then diluted with water (100 mL). The precipitate was filtered to yield the title compound as a off white solid.

$^1$H NMR (DMSO-d$_6$): δ 7.98 (1H, dd, J=6.5, 2.3 Hz), 7.92 (1H, dd, J=6.6, 2.4 Hz), 7.62 (1H, s), 7.36-7.45 (2H, m), 7.08 (1H, t, J=6.3 Hz), 6.72 (2H, s), 4.31 (2H, d, J=6.3 Hz).

Example 11

N-(benzo[b]thien-3-ylmethyl)-sulfamide (Compound #1)

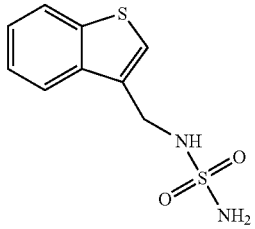

Thianaphthene-3-carboxaldehyde (5 g, 30.8 mmol) was dissolved in THF (50 mL). Sulfamide (12.22 g, 123.30 mmoles) and sulfamic acid (0.29 g, 3.08 mmoles) were added and the reaction mixture heated to 45° C. for 18 h. The reaction mixture was then cooled to room temperature and filtered through a sintered glass funnel. The resulting solution was treated with lithium borohydride (2.0 M in THF, 5 mL, 10 mmol) via addition funnel. After addition (5 minutes) the reaction mixture was stirred for 1 hour. 1N HCl (20 mL, 20 mmol) was added and the reaction mixture concentrated to remove THF. The resulting suspension was treated with water (100 mL) and vigorously stirred. The resulting solid was filtered and dried to yield the title compound as a light pink solid.

$^1$H NMR (DMSO-d$_6$): δ 7.98 (1H, dd, J=6.5, 2.3 Hz), 7.92 (1H, dd, J=6.6, 2.4 Hz), 7.62 (1H, s), 7.36-7.45 (2H, m), 7.08 (1H, t, J=6.3 Hz), 6.72 (2H, s), 4.31 (2H, d, J=6.3 Hz).

Example 12

1-Aminosulfonyl-4-phenyl-piperidine (Compound #31)

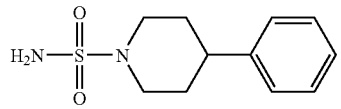

4-Phenyl-piperidine (10 g, 62 mmol) was dissolved in dioxane (100 mL). Sulfamide (23.8 g, 248 mmol) was then added and the reaction mixture heated to 100° C. for 14 h. The reaction mixture was then cooled to room temperature, quenched by addition of 1N HCl and then concentrated to remove dioxane. The product was extracted with ethyl acetate (100 mL), dried (Na$_2$SO$_4$), filtered and concentrated to yield the title compound as a light brown solid.

$^1$H NMR (DMSO-d$_6$): δ 7.35-7.15 (5H, m), 7.92 (1H, s), 6.76 (1H, s), 3.58 (2H, d, J=12.2 Hz), 2.68-2.50 (3H, m), 1.85 (2H, d, J=10.7 Hz), 1.68 (2H, dt, J=12.2, 12.2 Hz).

Example 13

4-Phenyl-piperidine-1-sulfonic acid (benzo[b]thiophen-3-ylmethyl)-amide (Compound #32)

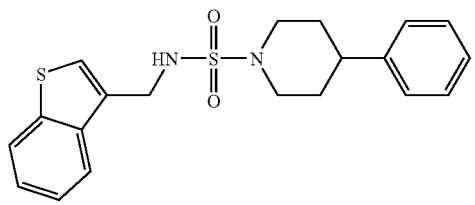

4-Phenyl-piperidine-1-sulfonic acid amide (1.5 g, 6.24 mmol) was dissolved in ethanol (20 mL). Benzo[b]thiophene-3-carbaldehyde (1.0 g, 6.24 mmol) was then added and the reaction mixture was warmed to 45° C. overnight. The reaction mixture was cooled to room temperature and then treated with sodium borohydride (0.2 g, 5.29 mmol). The reaction was then quenched by addition of 1N HCl. The reaction mixture was stirred overnight. The product precipitated from solution and was removed by vacuum filtration to yield the title compound as a white solid.

$^1$H NMR (DMSO-d$_6$): δ 7.99 (2H, q, J=12.0, 7.7 Hz), 7.86 (1H, dd, J=5.0 Hz), 7.66 (1H, s), 7.42 (2H, dt, J=14.0, 6.7 Hz), 7.35-7.24 (3H, m), 7.24-7.09 (2H, m), 4.37 (2H, d, J=5.8 Hz), 3.56 (2H, d, J=11.5 Hz), 2.75-2.59 (3H, m), 1.68 (2H, d, J=13.5 Hz), 1.31 (2H, dd, J=25.0, 13.5 Hz).

Example 14

Recrystallizaton of N-[(Benzo[b]thiophen-3-yl)methyl]sulfamide from Water

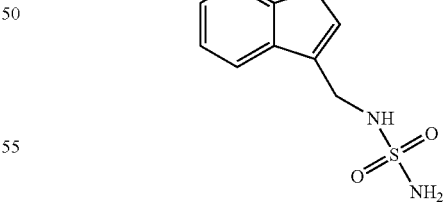

A 30 gal reactor was charged with crude N-[(benzo[b]thiophen-3-yl)methyl]sulfamide (470 g; 1.94 moles) followed by addition of water (25 L). The stirred mixture was heated to reflux and the heating was maintained until dissolution of the solid occurred. At this point the solution was hot filtered under pressure through an inline filter to a receiving vessel (20 gal) over a period of 30 minutes. The solution was then cooled to room temperature, over 2.5 h. The resulting solid was collected by filtration and rinsed with water, then air-dried under vacuum overnight to yield the title compound as a white solid.

Example 15

Recrystallizaton of N-[(Benzo[b]thiophen-3-yl)methyl]sulfamide from MTBE/Water

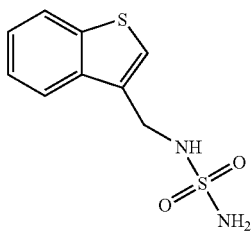

A 4 L Erlenmeyer flask was charged with crude N-[(benzo[b]thiophen-3-yl)methyl]sulfamide (720 g; 2.97 moles) followed by addition of methyl tert-butyl ether (2.5 L) and water (80.0 mL, 4.44 mole) and the mixture was heated slowly to reflux. The resulting solution was hot filtered through a pad of CELITE® into a 5 L four-necked reaction flask pre-warmed to 40° C. and equipped with an overhead stirrer, heating mantle, temperature control unit and vacuum adapter. The filter pad was washed with methyl tert-butyl ether (40 mL). After filtration the filtrate was allowed to cool slowly. When the temperature reached 60° C., the solution was seeded with a small amount of pure product, which induced crystallization of product shortly thereafter. Slow cooling was continued to room temperature and the mixture was maintained at room temperature overnight. The mixture was further cooled in an ice bath to 5° C. and the solid was collected by filtration, then air-dried to yield the title compound as a crystalline product DSC m.p. 106.8° C.

Elemental analysis calculated for $C_9H_{10}N_2O_2S_2$:

Calculated: C, 44.61; H, 4.16; N, 11.56; O, 13.21; S; KF: 26.47%

Measured: C, 44.43; H, 3.87, N, 11.57, S; KF 26.23%

Example 16

In Vivo Assay

Maximal Electroshock Test (MES)

Anticonvulsant activity was determined using the MES test, run according to the procedure described in detail below. Swinyard E A, Woodhead J H, White H S, Franklin M R. Experimental selection, quantification, and evaluation of anticonvulsants. In Levy R H, et al., eds. *Antiepileptic Drugs*. 3rd ed. New York: Raven Press, 1989:85-102

CF-1 male albino mice (25-35 g) were fasted for 16 hours before testing. Mice were randomly selected into control and test groups, with the animals dosed with vehicle or test compound, at varying concentrations, respectively. On the study date, at 30 minutes prior to shock, the mice were orally dosed with vehicle (0.5% methylcellulose) or test compound (100-300 mg/kg). Seizures were induced by trans-corneal electric shock using a 60-Hz alternating current, 50 mA, delivered for 0.2 sec. The mice in the test groups were subjected to electrical stimulus at time intervals between 15 minutes and 4 hours following administration of test compound. The shock resulted in an immediate full body tonic extension. The test was complete when the entire course of the convulsion has been observed (typically, less than 1 minute after electrical stimulation), and the mice were then immediately euthanized by carbon dioxide inhalation.

Abolition of the full body tonic extensor component of the seizure was taken as the endpoint of the test. Absence of this component indicated that the test compound had the ability to prevent the spread of seizure discharge through neural tissue. The $ED_{50}$ value of the test compound (calculated when appropriate) was the calculated dose required to block the hind limb tonic-extensor component of the MES-induced seizure in 50% of the rodents tested. A probit analysis was used to calculate the $ED_{50}$ and 95% fiducial limits (FL).

Representative compounds of the present invention were tested according to the procedure described above, with results as listed in Table 3 below. Results are listed as (number of mice with full body tonic extension prevented)/(total number of mice tested) (@ a given time).

TABLE 3

| | MES Activity | |
| --- | --- | --- |
| ID No. | MES @ 100 mpk | MES @ 300 mpk |
| 1 | 1/5 (0.5 h) | |
| | 3/5 (2 h) | |
| | 2/5 (4 h) | |
| 7 | inactive | 5/5 (0.5 hr) |
| | | 0/5 (2 hr) |
| | | 0/5 (4 hr) |
| 13 | 4/5 (0.5 h) | |
| | 0/5 (2 h) | |
| | 0/5 (4 h) | |
| 15 | | 0/3 (0.5 hr) |
| | | 0/3 (2 hr) |
| | | 1/3 (4 hr) |
| 17 | | 0/3 (0.5 hr) |
| | | 0/3 (2 hr) |
| | | 1/3 (4 hr) |
| 18 | | 0/3 (0.5 hr) |
| | | 2/3 (2 hr) |
| | | 0/3 (4 hr) |

Example 17

Prophetic

As a specific embodiment of an oral composition, 100 mg of the Compound #1 prepared as in Example 1 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A process for the preparation of a sulfamide derivative, comprising reacting an aldehyde with a substituted or unsubstituted sulfamide, in the presence of an acid or TMSCI, in a suitable organic solvent, to yield the corresponding sulfonylimine; reducing or hydrogenating the sulfonylimine, in a suitable organic solvent, to yield the corresponding sulfamide derivative.

2. The process of claim 1 wherein the sulfonylimine is reduced to the corresponding sulfamide derivative.

3. A process for the preparation of a compound of formula (I)

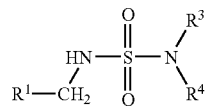

wherein $R^1$ is selected from the group consisting of alkyl, carbocyclyl, aryl, heteroaryl and heterocycloalkyl; wherein the alkyl, carbocyclyl, aryl, heteroaryl and heterocycloalkyl is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

$R^3$ and $R^4$ are each independently selected from the group consisting of alkyl, carbocyclyl, aryl, heteroaryl and heterocycloalkyl; wherein the alkyl, carbocyclyl, aryl, heteroaryl and heterocycloalkyl is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

alternatively, $R^3$ and $R^4$ are taken together with the nitrogen atom to which they are bound to form a monocyclic or bicyclic, saturated, partially unsaturated, partially aromatic or aromatic ring structure; wherein the ring structure is optionally substituted with one or more substituents independently selected from halogen, alkyl, alkoxy, hydroxy, carboxy, halogenated alkyl, halogenated alkoxy, cyano, nitro, amino, alkylamino, dialkylamino, amido, alkylamido, dialkylamindo, alkoxycarbonyl and aryloxycarbonyl;

or a pharmaceutically acceptable salt thereof;

comprising

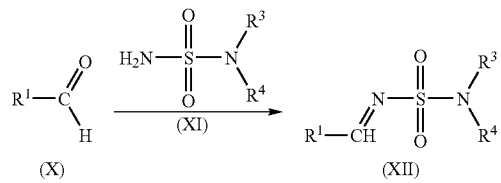

reacting a compound of formula (X) with a compound of formula (XI), in the presence of an acid or TMSCI, in a suitable organic solvent, to yield the corresponding compound of formula (XII);

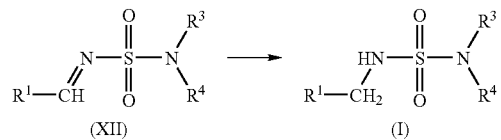

reducing or hydrogenating the compound of formula (XII), in a suitable organic solvent, to yield the corresponding compound of formula (I).

4. The process of claim 3, wherein the compound of formula (XII) is reduced to the corresponding compound of formula (I).

5. The process of claim 4, wherein the compound of formula (XII) is reduced by reacting with $Na(OAc_3)BH$ or $LiBH_4$ to yield the corresponding compound of formula (I).

* * * * *